United States Patent [19]

Mitamura et al.

[11] Patent Number: 4,820,868

[45] Date of Patent: Apr. 11, 1989

[54] PROCESS FOR PREPARATION OF NAPHTHALENE-2,6-DICARBOXYLIC ACID DIALKALI METAL SALTS

[75] Inventors: Shuichi Mitamura; Koichi Fujishiro; Hiroharu Inoue, all of Kawasaki, Japan

[73] Assignee: Nippon Steel Corporation, Tokyo, Japan

[21] Appl. No.: 912,957

[22] Filed: Sep. 29, 1986

[30] Foreign Application Priority Data

Sep. 30, 1985 [JP] Japan .................................. 60-215179
Oct. 31, 1985 [JP] Japan .................................. 60-242845

[51] Int. Cl.$^4$ ........................................... C07C 51/353
[52] U.S. Cl. .................................... 562/482; 562/423; 562/481; 562/488
[58] Field of Search ................ 562/481, 488, 482, 423

[56] References Cited

U.S. PATENT DOCUMENTS

| | | | |
|---|---|---|---|
| 2,823,231 | 2/1958 | Raecke et al. | 562/481 |
| 3,043,846 | 4/1962 | Blaser et al. | 562/481 X |
| 3,487,106 | 12/1969 | Patton et al. | 562/481 |
| 3,641,130 | 2/1972 | Kuper | 562/481 |
| 3,781,341 | 12/1973 | Wu et al. | 562/481 |

FOREIGN PATENT DOCUMENTS 1940319 8/1969 Fed. Rep. of Germany .

*Primary Examiner*—Werren B. Lone
*Assistant Examiner*—Vera C. Clarke

[57] ABSTRACT

Disclosed is a process for the preparation of a naphthalene-2,6-dicarboxylic acid dialkali metal salt which comprises heating an alkali metal salt of naphthoic acid and/or a dialkali metal salt of naphthalene-dicarboxylic acid under pressure with carbon dioxide gas in the presence of a catalyst, wherein an aprotic polycyclic aromatic compound having 2 or 3 rings is used as a reaction medium. Naphthalene-2,6-dicarboxylic acid dialkali metal salt can be obtained in high yield and selectivity with a good reproducibility of the reaction.

7 Claims, No Drawings

PROCESS FOR PREPARATION OF NAPHTHALENE-2,6-DICARBOXYLIC ACID DIALKALI METAL SALTS

BACKGROUND OF THE INVENTION (1) Field of the Invention

The present invention relates to a process for the preparation of a naphthalene-2,6-dicarboxylic acid dialkali metal salt. A naphthalene-2,6-dicarboxylic acid dialkali metal salt is easily converted to the corresponding carboxylic acid, tht is, naphthalene-2,6-dicarboxylic acid, by acidification. Recently, this naphthalene-2,6-dicarboxylic acid has attracted attention as the acid component of the starting materials for the preparation of a heat-resistant polyester, and is an industrially valuable compound.

(2) Description of the Related Art

The so-called Henkel process is known as one process for the preparation of a naphthalene-2,6-dicarboxylic acid dialkali metal salt. According to this process, an alkali metal salt of naphthalene-monocarboxylic acid (that is, naphthoic acid), a dialkali metal salt of naphthalene-dicarboxylic acid or a mixture thereof heated under pressure with carbon dioxide gas at a temperature higher than about 350° C., in the presence of a catalyst such as an oxide of cadmium, zinc or mercury or a halide, sulfate, carbonate or carboxylate thereof. From an alkali metal naphthoate, a naphthalene-2,6-dicarboxylic acid dialkali metal salt and naphthalene are formed by disproportionation reaction, and from a naphthalene-dicarboxylic acid dialkali metal salt, a naphthalene-2,6-dicarboxylic acid dialkali metal salt is selectively formed by rearrangement reaction [see (a) B. Raecke, Angew. Chem., 70, 1 (1958), (b) B. Raecke et al, Org. Syn. Coll. Vol. 5, 813 (1973), (c) Yamashita et al, Journal of Synthetic Organic Chemistry, Japan, 20, 501 (1962), (d) E. McNelis, J. Org. Chem., 30, 1209 (1965), (e) U.S. Pat. No. 2,823,231, and (f) Japanese Unexamined Patent Publication No. 51-10224].

All of the naphthoic acid alkali metal salt and naphthalene-dicarboxylic acid dialkali metal salt used as the starting material in the Henkel process and the naphthalene-2,6-dicarboxylic acid dialkali metal salt as the product of the Henkel process have a melting point higher than 400° C. These alkali metal salts are soluble in protonic solvents such as water and alcohols. However, at a reaction temperature higher than 350° C., as adopted in the Henkel process, a protonic solvent reacts with and decomposes the alkali metal salts, and therefore, the protonic solvent cannot be used as the reaction medium. Accordingly, where a naphthalene-2,6-dicarboxylic acid dialkali metal salt is prepared according to the Henkel process, a method has been adopted in which a powdery mixture of the starting material and catalyst is heated and reacted in the absence of a solvent under pressure with carbon dioxide gas and a solid product is obtained.

Since both the starting material and product are solid, this method is disadvantageous in comparison with the method using liquids in that the operations of charging the starting material in a reaction vessel and withdrawing the reaction product from the reaction vessel become complicated. Furthermore, we found that since the reaction is carried out in the absence of a solvet in the conventional method, the reproducibility of the reaction is not satisfactory and the yield and selectivity of the intended product are low.

More specifically, the reaction is ordinarily effected by heating the reaction vessel, and since the starting material and product are solids having a high melting point and no solvent is present, heat transfer in the reaction mixture is slow and heterogeneous. Accordingly, a certain portion of the reaction mixture is excessively heated and a large amount of carbonized matter is formed, while in another portion of the reaction mixture, heating is insufficient and the reaction is incomplete, with the result that a large amount of the starting material still remains or formation of isomers other than the intended naphthalene-2,6-dicarboxylic acid dialkali metal salt as a by-product becomes prominent. Accordingly, the yield of and selectivity to the intended naphthalene-2,6-dicarboxylic acid dialkali metal salt are reduced and the reproducibility of the reaction is not satisfactory.

SUMMARY OF THE INVENTION

It is a primary object of the present invention to solve the foregoing problems of the conventional process and provide a process in which an intended naphthalene-2,6-dicarboxylic acid dialkali metal salt can be obtained in a high yield and selectivity with a good reproducibility of the reaction.

In accordance with the present invention, there is provided a process for the preparation of a naphthalene-2,6-dicarboxylic acid dialkali metal salt which comprises heating at least one compound selected from the group consisting of alkali metal salts of naphthoic acid and dialkali metal salts of naphthalene-dicarboxylic acid under pressure with carbon dioxide gas in the presence of a csatalyst, wherein an aprotic polycyclic aromatic compound having 2 or 3 rings is used as a reaction medium, and the amount of the aprotic polycyclic aromatic compound is 0.5 to 10 times the amount of the starting material by weight.

DESCRIPTION OF THE PREFERRED EMBODIMENTS

The starting material used in the present invention is an alkali metal salt of naphthoic acid, a dialkali metal salt of naphthalene-dicarboxylic acid, or a mixture thereof. As the alkali metal salt of naphthoic acid, there may be used a 1-isomer, a 2-isomer, and a mixture thereof. As the dialkali metal salt of naphthalene-dicarboxylic acid, there may be used a 1,2-isomer, a 1,3-isomer, a 1,4-isomer, a 1,5-isomer, a 1,6-isomer, a 1,7-isomer, a 1,8-isomer, a 2,3-isomer, a 2,6-isomer, a 2,7isomer, or a mixture thereof. Among the foregoing isomers, the naphthalene-2,6-dicarboxylic acid dialkali metal salt is the intended compound of the present invention, but if the starting material containing a small proportion of this isomer or a crude mixture is used, the compound can be used as the starting material. As in the conventional Henkel process, a potassium salt gives good results as the alkali metal salt.

Any catalyst that can be used for disproportionation and rearrangement in the ordinary Henkel process can be used in the process of the present invention. Generally, a catalyst is selected from cadmium compounds, zinc compounds, and mercury compounds, and as typical examples, there can be mentioned oxides, halides, sulfates, carbonates, and carboxylates of these metals. As examples of the cadmium compound, there can be mentioned cadmium chloride, cadmium bromide, cadmium iodide, cadmium fluoride, cadmium oxide, cadmium carbonate, cadmium naphthoate, and cadmium naphthalenedicarboxylate. Cadmium compounds or mercury compounds are toxic and expensive, and therefore, from the industrial viewpoint, use of a zinc compound is preferred. As the zinc compound, there can be mentioned zinc halides such as zinc fluoride, zinc chloride, zinc bromide, and zinc iodide; zinc carboxylates such as zinc naphthoate and zinc naphthalene-dicarboxylate; zinc oxide, zinc carbonate; zinc sulfate; and mixtures thereof. Note, zinc naphthoate includes a 1-isomer, a 2-isomer, and a mixture thereof, and zinc naphthalenedicarboxylate includes a 1,2-isomer, a 1,3-isomer, a 1,4-isomer, a 1,5-isomer, a 1,6-isomer, a 1,7-isomer, a 1,8-isomer, a 2,3-isomer, a 2,6-isomer, a 2,7-isomer, and a mixture thereof.

Where a zinc compound as described above is used as the catalyst, if a metal halide is used as a co-catalyst, the catalytic activity is improved. As the metal halide, a metal chloride, a metal bromide, and a metal iodide are effective, and a metal bromide and a metal iodide have a very high effect and are especially preferred. These metal halides may be used singly or in the form of a mixture. As the metal of the metal halide, there can be mentioned various metals (exclusive of zinc) such as alkali metals and alkaline earth metals. In view of the low toxicity and easy recovery from the reaction mixture after completion of the reaction, an alkali metal halide is preferably. Moreover, for the reasons set forth below, it is especially preferable that a halide of the same alkali metal as that of the starting alkali metal salt be used. For example, when a sodium salt or potassium salt is used as the starting material, preferably a sodium halide or potassium halide is used.

As examples of the metal halide preferred from the foregoing viewpoint, there can be mentioned lithium chloride, sodium chloride, potassium chloride, cesium chloride, rubidium chloride, lithium bromide, sodium bromide, potassium bromide, cesium bromide, rubidium bromide, lithium iodide, sodium iodide, potassium iodide, cesium iodide, and rubidium iodide.

Note, the fact that the catalytic activity of a zinc compound as the catalyst is improved by addition of a metal halide as the co-catalyst is generally observed is not only the reaction where a reaction medium is used as in the process of the present invention but also in the reaction which is carried out in the absence of a solvent.

The catalyst is used in an amount of 0.5 to 20 mole%, preferably 1 to 10 mole%, based on the starting material. When the metal halide is used as the co-catalyst for the zinc compound catalyst, the metal halide is used in an amount of 0.5 to 20 mole%, preferably 1 to 10 mole%, based on the starting material. Note, in the following description, the catalyst and the co-catalyst are not particularly distinguished, but are inclusively called "catalyst".

Preferably the starting material is sufficiently mixed with the catalyst. For this purpose, there may be adopted any method in which the catalyst is added to an aqueous solution of the starting material, the mixture is sufficiently stirred, and water is removed by heating and distillation to obtain a mixture of the starting material and catalyst, any method in which the starting material and catalyst are sufficiently mixed and pulverized in a ball mill or the like, and any method in which the starting material and catalyst are separately pulverized sufficiently and are incorporated with stirring into a reaction medium for a polycyclic aromatic compound described below.

In the present invention, the starting material and catalyst are heated under pressure with carbon dioxide gas in a reaction medium. A substance which is stable and liquid under the reaction conditions is used as the reaction medium.

This substance may be a single compound or a mixture. In the present invention, disproportionation and/or rearrangement proceeds substantially at 350° to 500° C. Thus, a substance having a melting point not higher than 500° C. and a critical temperature not lower than 350° C. becomes liquid under certain reaction conditions and can be used as a reaction medium. We investigated substances having such melting and critical temperatures and a good stability under reaction conditions, and capable of improving the yield, and as a result, found that an aprotic polycyclic aromatic compound having 2 or 3 rings satisfies these requirements.

As the polycyclic aromatic compound, there can be mentioned naphthalene, methylnaphthalene, dimethylnaphthalene, biphenyl, methylbiphenyl, dimethylbiphenyl, diphenyl ether, dinaphthyl ether, terphenyl, anthracene, phenanethrene, and mixtures thereof. The polycyclic aromatic compound is used in an amount of 0.5 to 10 times, preferably 1 to 5 times, the amount of the starting material based on the weight.

The solubility of the starting material and catalyst of the present invention in the polycyclic aromatic compound is extremely low. Accordingly, the starting material and catalyst are generally supplied in the form of a slurry dispersed in the polycyclic aromatic compound. To improve the dispersion state of the starting material and catalyst, preferably the starting material and catalyst or a mixture thereof are pulverized in advance.

The presence of water extremely inhibits the reaction of the present invention. Accordingly, when carrying out the reaction of the present invention, good results are obtained if the starting material, catalyst, and polycyclic aromatic compound are dehydrated and dried in advance. Methods customarily used for the dehydration and drying may be adopted in this case. For example, drying under hot air current and vacuum drying with heating may be adopted for the starting material and catalyst, and distillation purification may be adopted for the polycyclic aromatic compound. Furthermore, the following method may be adopted.

More specifically, a slurry comprising a mixture of the starting material, catalyst and polycyclic aromatic compound is heated to remove a part of the slurry by distillation. Where water is contained, the water is distilled off as an initial fraction and can be easily removed from the mixture. This method is based on the fact that the polycyclic aromatic compound is a high-boiling-point compound having a boiling point higher than 200° C. under atmospheric pressure and the difference of the boiling point between this compound and water is large.

The starting material, catalyst, and polycyclic aromatic compound can be introduced into a reaction vessel independently or in the form of a mixture. When a mixture of the three components is introduced, in accordance with one preferred embodiment of the present invention, a method is adopted in which the mixture is heated at a temperature higher than the melting point of the polycyclic aromatic compound to form a slurry and the slurry is introduced into the reaction vessel.

The starting material, catalyst, and polycyclic aromatic compound thus introduced into the reaction vessel are heated under pressure with carbon dioxide gas to cause the reaction. To uniformalize the dispersion of the starting material and catalyst, and uniformalize the conduction of heat, preferably the content in the reaction vessel is stirred. Either a batchwise reactor or a continuous reactor may be used for the reaction, and the reaction is not substantially influenced by the type of the reaction vessel.

The pressure of carbon dioxide gas is 5 to 100 kg/cm$^2$.G, preferably 10 to 70 kg/cm$^2$.G, as calculated as the pressure at 100° C. In principle, the reaction temperature is substantially the same as the reaction temperature adopted in the conventional Henkel process. Namely, the reaction temperature is ordinarily 350° to 500°, although the reaction temperature is changed to some extent according to the kinds of starting material and catalyst. To accelerate the reaction and suppress the occurrence of side reactions such as the formation of carbonized matters, preferably the reaction temperature is 380° to 470° C. The reaction time is ordinarily 5 minutes to 4 hours, although the reaction time is changed according to the reaction temperature.

After completion of the reaction, the reaction mixture is withdrawn from the reaction vessel and subjected to separation and purification. As a simple withdrawal method utilizing the characteristics of the present invention, there can be mentioned a method in which the reaction mixture is maintained at a temperature higher than the melting point of the polycyclic aromatic compound and the reaction mixture is withdrawn in the form of a slurry.

If an organic solvent such as toluene or xylene and water are added to the withdrawn reaction mixture, the polycyclic aromatic compound is dissolved in the organic solvent while the obtained naphthalene-2,6-dicarboxylic acid dialkali metal salt is dissolved in water. The catalyst such as a zinc compound or cadmium compound and carbonized matters formed as the by-product are insoluble in both the organic solvent and water. The respective components are separated by filtration or liquid layer separation, and an aqueous solution of the naphthalene-2,6-dicarboxylic dialkali metal salt is recovered. Naphthalene-2,6-dicarboxylic acid can be obtained from this aqueous solution by acidification with hydrochloric acid or the like according to customary procedures.

The present invention will now be described in detail with reference to the following examples and comparative examples.

EXAMPLE 1 THROUGH 14

To 10 g of dipotassium naphthalene-1,8-dicarboxylate, that is, dipotassium-1,8-naphthalate, were added predetermined amounts of zinc chloride and potassium iodide, and they were mixed and pulverized. The mixture was charged in an autoclave having an inner volume of 200 ml and provided with a stirrer.

A predetermined amount of a polycyclic aromatic compound was added and the inner atmosphere of the autoclave was replaced with carbon dioxide gas and then, the inner pressure of the autoclave was raised to a predetermined pressure (initial pressure shown in Table 1) by introduction of carbon dioxide gas. The temperature was then elevated to a predetermined reaction temperature at a rate of 4° C./min while the mixture in the autoclave was stirred, and the mixture was stirred at the reaction temperature for 1 hour to complete the reaction.

After completion of the reaction, 200 ml of toluene and 200 ml of water were added to the reaction mixture and the mixture was sufficiently stirred. Solids insoluble in either the water layer or the toluene layer were removed by filtration, and then the water layer was separated. a part of the water layer was sampled, and the amount of dipotassium naphthalene-2,6-dicarboxylate was measured by the internal standard method using high performance liquid chromatography, and the yield of dipotassium naphthalene-2,6-dicarboxylate was calculated.

As the polycyclic aromatic compound, there were used naphthalene, methylnaphthalene, biphenyl, a mixture comprising diphenyl ether and biphenyl at a ratio of about 7/3, and phenanthrene, respectively.

The obtained results are shown in Table 1.

COMPARATIVE EXAMPLE 1

The procedures of Example 1 were performed in the same manner except that naphthalene as the polycyclic aromatic compound was not added. The obtained results are shown in Table 1.

TABLE 1

| | Catalyst (mole %) | Kind and amount of polycyclic aromatic compound | (g) | Reaction pressure (kg/cm$^2$ · G) Initial pressure | Final pressure | Reaction temperature (°C.) | Yield of dipotassium naphthalene-2,6-dicarboxylate (%) |
|---|---|---|---|---|---|---|---|
| Example 1 | ZnCl$_2$(8)—KI(8) | naphthalene | 20 | 40 | 70 | 450 | 70.0 |
| Example 2 | " | " | 50 | 40 | 70 | 450 | 68.0 |
| Example 3 | " | " | 30 | 40 | 70 | 450 | 69.1 |
| Example 4 | " | " | 30 | 40 | 72 | 460 | 70.6 |
| Example 5 | " | " | 30 | 40 | 63 | 410 | 59.8 |
| Example 6 | " | " | 30 | 60 | 75 | 450 | 62.1 |
| Example 7 | " | " | 30 | 20 | 40 | 450 | 63.6 |
| Example 8 | ZnCl$_2$(8)—KI(4) | " | 30 | 40 | 70 | 450 | 70.7 |
| Example 9 | ZnCl$_2$(4)—KI(4) | " | 30 | 40 | 70 | 450 | 68.7 |
| Example 10 | ZnCl$_2$(1)—KI(1) | " | 30 | 40 | 70 | 450 | 61.0 |
| Example 11 | ZnCl$_2$(8)—KI(8) | methylnaphthalene | 30 | 40 | 65 | 450 | 65.2 |
| Example 12 | " | biphenyl | 30 | 40 | 61 | 450 | 62.6 |
| Example 13 | " | diphenyl ether/biphenyl (7:3) | 30 | 40 | 55 | 450 | 60.4 |
| Example 14 | " | phenanthrene | 30 | 40 | 64 | 450 | 61.3 |
| Comparative Example 1 | " | not added | | 40 | 68 | 450 | 53.8 |

EXAMPLES 15 THROUGH 25

To 10.0 g of dipotassium-1,8-naphthalate was added a predetermined amount of a catalyst shown in Table 2, and the reaction was carried out in the presence of 30 g of naphthalene in the same manner as in Example 3. The obtained results are shown in Table 2.

COMPARATIVE EXAMPLES 2 THROUGH 8

The procedures of Examples 15, 17, 19 and 22 through 25 were performed respectively in the same manner except that naphthalene was not added. The obtained results are shown in Table 2.

TABLE 2

| Catalyst (mole %) | Yield of dipotassium naphthalene-2,6-dicarboxylate (%) | | | |
|---|---|---|---|---|
| | Presence of naphthalene [Example No.] | | Absence of naphthalene [Comparative Example No.] | |
| $ZnI_2(8)$ | 69.6 | [15] | 54.7 | [2] |
| $ZnBr_2(8)$ | 63.5 | [16] | — | |
| $ZnCl_2(8)$ | 62.3 | [17] | 48.9 | [3] |
| $ZnCl_2(1)$ | 49.8 | [18] | — | |
| $ZnCl_2(8)$ - KBr(8) | 64.8 | [19] | 53.7 | [4] |
| $ZnCl_2(8)$ - NaI(8) | 69.7 | [20] | — | |
| $ZnBr_2(8)$ - KI(8) | 70.2 | [21] | — | |
| ZnO(8) | 41.1 | [22] | 36.7 | [5] |
| ZnO(8) - KI(8) | 45.8 | [23] | 37.2 | [6] |
| $CdI_2(8)$ | 68.3 | [24] | 56.2 | [7] |
| $CdCl_2(8)$ | 68.7 | [25] | 57.8 | [8] |

EXAMPLES 26 THROUGH 35

The 10.0 g of dipotassium-1,8-naphthalate was added a predetermined amount of zinc 1,8-naphthalate, and after or without addition of a predetermined amount of potassium iodide or potassium chloride, the mixture was pulverized and blended by a ball mill and the mixture was charged into an autoclave having an inner capacity of 200 ml and provided with a stirrer. Then, a predetermined amount of naphthalene was added and the mixture was heated at 100° C. The inner atmosphere of the autoclave was replaced with carbon dioxide gas, and then carbon dioxide gas was raised to a predetermined pressure (initial pressure shown in Table 3). The temperature was elevated to a predetermined reaction temperature at a rate of 4° C./min while the mixture in the autoclave was stirred, and the mixture was stirred at the reaction temperature for a predetermined time. The work-up was carried out in the same manner as in Examples 1 through 14, and the product was determined by high performance liquid chromatography. The yield of dipotassium naphthalene-2,6-dicarboxylate was calculated according to the formula:

$$\text{Yield (\%)} = \frac{A}{B + C} \times 100$$

wherein A stands for the amount (mole) of formed dipotassium naphthalene-2,6-dicarboxylate, B stands for the amount (mole) of charged dipotassium 1,8-naphthalate, and C stands for the amount (mole) of charged zinc 1,8-naphthalate.

COMPARATIVE EXAMPLES 9 AND 10

The procedures of Examples 26 and 34 were repeated in the same manner except that naphthalene was not added.

The obtained results are shown in Table 3.

EXAMPLE 36

To 10.0 g of dipotassium 1,8-naphthalate was added 8,7 mole%, based on dipotassium 1,8-naphthalate, of potassium iodide and they were sufficiently mixed and pulverized in a ball mill. The mixture was charged in an autoclave having an inner capacity of 200 ml and provided with a stirrer. Then, 8.7 mole% of powdery zinc, 1,8-naphthalate and 30 g of naphthalene were added. The reaction followed by the work-up and the product analysis were carried out in the same manner as in Example 29. The obtained results are shown in Table 3.

TABLE 3

| | Catalyst (mole %) | Amount of naphthalene (g) | Reaction pressure ($kg/cm^2 \cdot G$) | | Reaction temperature (°C.) | Reaction time (hour) | Yield of dipotassium naphthalene-2,6-dicarboxylate (%) |
|---|---|---|---|---|---|---|---|
| | | | Initial pressure | Final pressure | | | |
| Example 26 | zinc 1,8-naphthalate(8) | 30 | 40 | 70 | 450 | 1 | 57.1 |
| Comparative Example 9 | zinc 1,8-naphthalate(8) | not added | 40 | 66 | 450 | 1 | 39.6 |
| Example 27 | zinc 1,8-naphthalate (8.7)-KI(8.7) | 30 | 60 | 85 | 450 | 1 | 66.2 |
| Example 28 | zinc 1,8-naphthalate (8.7)-KI(8.7) | 30 | 50 | 77 | 450 | 1 | 68.5 |
| Example 29 | zinc 1,8-naphthalate (8.7)-KI(8.7) | 30 | 40 | 68 | 450 | 1 | 70.3 |
| Example 30 | zinc 1,8-naphthalate (8.7)-KI(8.7) | 30 | 30 | 59 | 450 | 1 | 65.3 |
| Example 31 | zinc 1,8-naphthalate (8.7)-KI(4.2) | 30 | 40 | 70 | 450 | 1 | 64.5 |
| Example 32 | zinc 1,8-naphthalate (4.3)-KI(4.3) | 30 | 40 | 70 | 450 | 1 | 67.5 |
| Example 33 | zinc 1,8-naphthalate (8.7)-KI(12) | 30 | 40 | 70 | 450 | 1 | 69.5 |
| Example 34 | zinc 1,8-naphthalate (8)-KI(8) | 30 | 40 | 70 | 450 | 1 | 67.0 |
| Comparative Example 10 | zinc 1,8-naphthalate (8)-KI-(8) | not added | 40 | 68 | 450 | 1 | 51.8 |
| Example 35 | zinc 1,8-naphthalate (8)-KCl(8) | 30 | 40 | 70 | 450 | 1 | 63.1 |
| Example 36* | zinc 1,8-naphthalate | 30 | 40 | 68 | 450 | 1 | 68.3 |

TABLE 3-continued

| Catalyst (mole %) | Amount of naphthalene (g) | Reaction pressure (kg/cm² · G) Initial pressure | Reaction pressure (kg/cm² · G) Final pressure | Reaction temperature (°C.) | Reaction time (hour) | Yield of dipotassium naphthalene-2,6-dicarboxylate (%) |
|---|---|---|---|---|---|---|
| (8.7)-KI(8.7) | | | | | | |

Note
*different from Example 29 in manner of charging starting material, catalyst and naphthalene.

EXAMPLES 37 THROUGH 45

Reaction was carried out in the presence of 30 g of naphthalene in the same manner as described in Example 3 except that a predetermined amount of dipotassium naphthalene-2,3-dicarboxylate, potassium 2-naphthoate, a mixture comprising dipotassium 1,8-naphthalate and potassium 2-naphthoate (mixing weight ratio=1/1) or a mixture of 2,6-, 2,7-, 1,6-, 1,7- and 1,3-isomers of dipotassium naphthalene-dicarboxylate was used as the starting material instead of dipotassium 1,8-naphthalate and a predetermined amount of a catalyst shown in Table 4 was used. The obtained results are shown in Table 4.

COMPARATIVE EXAMPLES 11 THROUGH 15

The procedures of Example 37, 39, 40, 42 and 44 were performed respectively in the same manner except that naphthalene was not added. The obtained results are shown in Table 4.

TABLE 4

| Starting material | Catalyst (mole %) | Yield of dipotassium naphthalene-2,6-dicarboxylate (%) Presence of naphthalene [Example No.] | Yield of dipotassium naphthalene-2,6-dicarboxylate (%) Absence of naphthalene [Comparative Example No.] |
|---|---|---|---|
| dipotassium naphthalene-2,3-dicarboxylate | $ZnCl_2(8)$—KI(8) | 70.9 [37] | 59.5 [11] |
| dipotassium naphthalene-2,3-dicarboxylate | $ZnCl_2(8)$ | 63.7 [38] | — |
| potassium 2-naphthoate | $ZnCl_2(8)$—KI(8) | 31.6 [39] | 24.8 [12] |
| potassium 2-naphthoate | $CdI_2(8)$ | 40.4 [40] | 37.0 [13] |
| potassium 2-naphthoate | $ZnCl_2(8)$ | 30.4 [41] | — |
| dipotassium 1,8-naphthalate/ potassium 2-naphthoate (1/1) | $ZnCl_2(8)$—KI(8) | 53.3 [42] | 46.7 [14] |
| dipotassium 1,8-naphthalate/ potassium 2-naphthoate (1/1) | $ZnCl_2(8)$ | 47.7 [43] | — |
| isomer mixture of dipotassium naphthalene-dicarboxylate | $ZnCl_2(8)$—KI(8) | 71.6 [44] | 58.2 [15] |
| isomer mixture of dipotassium naphthalene-dicarboxylate | $ZnCl_2(8)$ | 62.5 [45] | — |

I claim:

1. An improvement in a process for the preparation of a naphthalene-2,6-dicarboxylic acid dialkali metal salt which comprises heating an alkali metal salt of naphthalene-dicarboxylic acid selected from the group consisting of a 1,2-isomer, a 1-3 isomer, a 1,4-isomer, a 1,5-isomer, a 1,6-isomer, a 1,7-isomer, a 1,8-isomer, a 2,3-isomer, a 2,7-isomer, or a mixture thereof, under pressure with carbon dioxide gas in the presence of a catalyst, the improvement comprising using naphthalene as a reaction medium, wherein the amount of the naphthalene is 0.5 to 10 times the amount of the starting material by weight.

2. A process according to claim 1, wherein the catalyst is a metal compound selected from the group consisting of cadmium compounds, zinc compounds, and mercury compounds.

3. A process according to claim 1, wherein the catalyst is a combination of a zinc compound and a metal halide, exclusive of a zinc halide.

4. A process according to claim 3, wherein the metal halide is selected from the group consisting of metal chlorides, metal bromides and metal iodides.

5. A process according to claim 3, wherein the metal halide is an alkali metal halide.

6. A process according to claim 1, wherein the starting compound is dipotassium naphthalene-dicarboxylate.

7. A process according to claim 1, wherein the heating temperature is 350° to 500° C.

* * * * *